US011213811B2

(12) United States Patent
Wang et al.

(10) Patent No.: US 11,213,811 B2
(45) Date of Patent: Jan. 4, 2022

(54) PREPARATION METHOD FOR OLEFIN EPOXIDATION CATALYST AND APPLICATIONS THEREOF

(71) Applicant: WANHUA CHEMICAL GROUP CO., LTD., Shandong (CN)

(72) Inventors: Lei Wang, Shandong (CN); Tongji Wang, Shandong (CN); Fei Ye, Shandong (CN); Lichao Yang, Shandong (CN); Guangquan Yi, Shandong (CN); Jiaoying Cui, Shandong (CN); Naibo Chu, Shandong (CN); Yuan Li, Shandong (CN); Weiqi Hua, Shandong (CN)

(73) Assignee: WANHUA CHEMICAL GROUP CO., LTD., Shandong (CN)

( * ) Notice: Subject to any disclaimer, the term of this patent is extended or adjusted under 35 U.S.C. 154(b) by 57 days.

(21) Appl. No.: 16/484,574

(22) PCT Filed: May 24, 2018

(86) PCT No.: PCT/CN2018/088175
§ 371 (c)(1),
(2) Date: Jan. 27, 2020

(87) PCT Pub. No.: WO2018/214931
PCT Pub. Date: Nov. 29, 2018

(65) Prior Publication Data
US 2020/0147599 A1    May 14, 2020

(30) Foreign Application Priority Data

May 25, 2017   (CN) .......................... 201710379007.2

(51) Int. Cl.
B01J 37/02        (2006.01)
B01J 21/06        (2006.01)
(Continued)

(52) U.S. Cl.
CPC ......... B01J 37/0201 (2013.01); B01J 21/063 (2013.01); B01J 37/0236 (2013.01);
(Continued)

(58) Field of Classification Search
CPC . B01J 21/063; B01J 21/08; B01J 23/10; B01J 35/02; B01J 35/1019; B01J 35/1042;
(Continued)

(56) References Cited

U.S. PATENT DOCUMENTS 4,367,342 A * 1/1983 Wulff ....................... B01J 21/06
                                                   549/529
6,114,552 A    9/2000 Han et al.
2013/0116454 A1  5/2013 Buijink

FOREIGN PATENT DOCUMENTS

CN    104226312 A    1/2014
CN    106334583 A    1/2017
CN    106378122 A    2/2017

OTHER PUBLICATIONS

International Search Report for corresponding international Application No. PCT/CN2018/088175 dated Aug. 9, 2018.
(Continued)

Primary Examiner — Brian A McCaig
(74) Attorney, Agent, or Firm — Michael Best and Friedrich LLP

(57) ABSTRACT

Disclosed in the present invention are a preparation method for an olefin epoxidation catalyst and applications thereof. The method comprises: loading an auxiliary metal salt onto a silica gel carrier, and carrying out a drying treatment to the silica gel carrier; loading a titanium salt (preferably $TiCl_4$) onto the silica gel carrier by a chemical vapor deposition method; calcining to obtain a silica gel on which the auxiliary metal oxide and Ti species are loaded; obtaining an catalyst precursor (Ti-MeO—$SiO_2$ composite oxide) by water vapor washing; loading alkyl silicate (preferably tet-
(Continued)

raethyl orthosilicate) onto the surface of the catalyst precursor by a chemical vapor deposition method and calcining the catalyst precursor to obtain a Ti-MeO—$SiO_2$ composite oxide with the surface coated with a $SiO_2$ layer; and carrying out a silylanization treatment to obtain the catalyst. The catalyst can be applied to a chemical process of propylene epoxidation to prepare propylene oxide, and has an average selectivity to PO up to 96.7%, the method of the present invention and the applications thereof have industrial application prospects.

20 Claims, 1 Drawing Sheet

(51) Int. Cl.
    *B01J 37/08*     (2006.01)
    *C07D 301/19*     (2006.01)
    *B01J 21/08*     (2006.01)
    *C07D 303/04*     (2006.01)

(52) U.S. Cl.
    CPC ........... *B01J 37/0238* (2013.01); *B01J 37/08* (2013.01); *C07D 301/19* (2013.01); *B01J 21/08* (2013.01); *C07D 303/04* (2013.01)

(58) Field of Classification Search
    CPC   B01J 35/1047; B01J 35/1061; B01J 37/0201; B01J 37/0209; B01J 37/0236; B01J 37/0238; B01J 37/08; B01J 37/088; B01J 31/26; B01J 2229/32; C07D 301/19; C07D 303/04
    See application file for complete search history.

(56) References Cited

OTHER PUBLICATIONS

Yuan Chun et al., "Research for Chemical Vapor Deposition of Ethyl Orthosilicate on Zeolite", Journal of National Catalysis Conference, Nanjing University.
European Patent Office Extended Search Report for Application No. 18805296.3 dated Sep. 18, 2020 (8 pages).
Chinese Patent Office Action for Application No. 2017103790072 dated Mar. 25, 2019 (19 pages including English translation).
Chinese Patent Office Search Report for Application No. 2017103790072 dated Mar. 25, 2019 (4 pages including English translation).

* cited by examiner

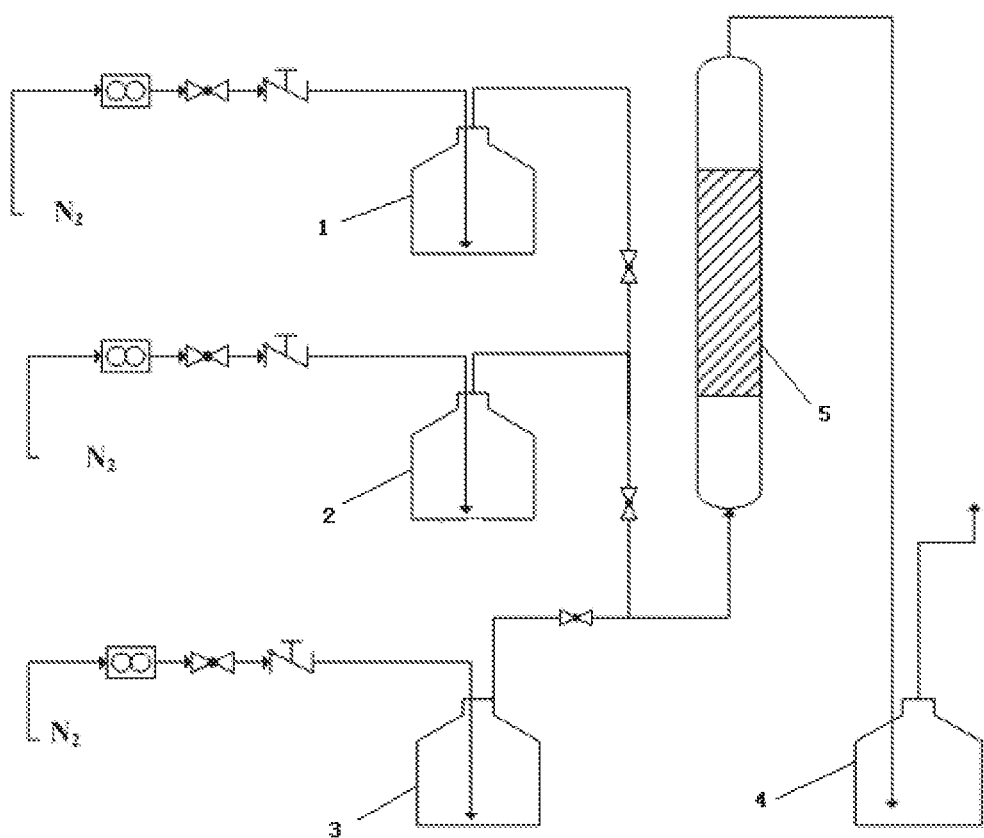

PREPARATION METHOD FOR OLEFIN EPOXIDATION CATALYST AND APPLICATIONS THEREOF

CROSS REFERENCE TO RELATED APPLICATIONS

This application is a national stage filing under 35 U.S.C. § 371 of International Patent Application No.: PCT/CN2018/088175, filed May 24, 2018, which claims priority to Chinese Patent Application No. 201710379007.2, filed May 25, 2017, the entire contents of all of which are hereby incorporated by reference herein.

TECHNICAL FIELD

The present disclosure relates to a preparation method for an olefin epoxidation catalyst, specifically a preparation method for a $SiO_2$—Ti-MeO—$SiO_2$ composite oxide catalyst and a catalyst prepared according to the method, and further relates to use of the catalyst in catalyzing propylene epoxidation to prepare propylene oxide.

BACKGROUND

Co-oxidation methods, also known as Halcon methods, are important methods for producing propylene oxide, comprising isobutane co-oxidation method (PO/TBA) and ethylbenzene co-oxidation method (PO/SM). First of all, peroxide is obtained by oxidizing isobutane or ethylbenzene respectively, then propylene oxide is obtained by oxidizing propylene, and tert-butyl alcohol or styrene is co-produced.

Co-oxidation methods overcome the disadvantages such as strong corrosiveness, large production of polluted water of the chlorohydrin method, and have advantages such as low product cost (co-products share the cost) and less environmental pollution. Co-oxidation methods have been developed rapidly around the world since the methods were industrialized in 1969. At present, the capacity of producing propylene oxide by a co-oxidation method accounts for about 55% of the total capacity in the world. In the co-oxidation methods, PO/SM process co-produces styrene, which is a chemical product produced in bulk and is an important monomer for synthesizing resin and rubber. Due to the relatively broad market of the co-product, this process is spreading faster and faster.

The PO/SM processes can be divided into homogeneous PO/SM processes and heterogeneous PO/SM processes according to the different catalysts used in the key procedures (epoxidation procedures) of the processes. The catalysts used in the epoxidation procedures of the heterogeneous PO/SM processes are Ti—$SiO_2$ composite oxide catalysts. The main steps of the preparation methods disclosed in U.S. Pat. No. 3,829,392 and US2003166951A1 as well as Chinese Patent Applications CN1894030A and CN1720100A are as follows: a silica gel carrier was dried first, and then using $N_2$ or other inert gases to introduce titanium halide vapor into a reaction tube to react with silica gel (this step is called a chemical vapor deposition), high temperature calcination, and finally a catalyst was prepared through steps such as water washing. The catalyst prepared by this method has problems such as the Ti active center is easily lost during use, the catalyst activity decreases rapidly and the catalyst has a short life.

In order to solve the above problems, it is necessary to seek a new preparation method for propylene epoxidation catalyst to reduce the loss of Ti active center and improve the service life of the catalyst.

SUMMARY OF THE DISCLOSURE

The object of the present disclosure is to provide a preparation method for an olefin epoxidation catalyst. The olefin epoxidation catalyst prepared by the preparation method of the present disclosure can reduce the loss of Ti active center during use and improve the service life of the catalyst.

In the present disclosure, the catalyst is obtained as follows: an auxiliary metal salt is loaded onto a silica gel carrier first, dried, and then a chemical vapor deposition is carried out, the thus obtained product is calcined to load Ti species, washed with water, then a chemical vapor deposition and calcination are carried out again to load a $SiO_2$ layer onto the surface of Ti-MeO—$SiO_2$, and finally a silylanization treatment is carried out. The catalyst prepared by the preparation method of the present disclosure can reduce the loss of the Ti active center and improve the service life of the catalyst during use, especially when applied for catalyzing propylene epoxidation to produce propylene oxide.

Another object of the present disclosure is to provide use of the catalyst (also referred to as a $SiO_2$—Ti-MeO—$SiO_2$ composite oxide catalyst) prepared by said method, the catalysts can be used as a catalyst for olefin epoxidation to produce an epoxide, especially a catalyst for propylene epoxidation to produce propylene oxide, and the catalyst not only has good catalyst activity, the catalyst also has high average selectivity to PO (propylene oxide).

In order to achieve the above objects, the present disclosure adopts the following technical solutions:

A preparation method for an olefin epoxidation catalyst, which comprises the following steps:

(1) loading an auxiliary metal salt onto a silica gel carrier to obtain a silica gel carrier A modified by the auxiliary metal salt; in some specific embodiments, the auxiliary metal salt can be loaded onto the silica gel carrier using a impregnation method, such as an incipient-wetness impregnation method;

(2) carrying out a drying treatment for the A obtained in step (1);

(3) carrying out a chemical vapor deposition for the dried A using a titanium salt vapor, preferably $TiCl_4$ vapor to obtain a silica gel B on which the auxiliary metal salt and the titanium salt, preferably $TiCl_4$ are loaded; in some preferred embodiments, in step (3), the dried A is charged into a reaction tube (preferably a fixed bed reactor), and preferably nitrogen is used to introduce the titanium salt vapor into the reaction tube to carry out the chemical vapor deposition;

(4) calcining the B obtained in step (3) to obtain a silica gel C on which the auxiliary metal salt and Ti species are loaded; preferably, the calcination is carried out in $N_2$ atmosphere;

(5) carrying out a water vapor washing for the C obtained in step (4), the product obtained by washing is referred to as Ti-MeO—$SiO_2$ composite oxide;

(6) carrying out another vapor deposition for the Ti-MeO—$SiO_2$ composite oxide obtained in step (5) using an alkyl silicate vapor, preferably tetraethyl orthosilicate vapor to obtain the Ti-MeO—$SiO_2$ composite oxide D having a silicon-containing compound loaded on the surface of the composite oxide; preferably, the vapor deposition is carried out in a reaction tube, and the alkyl silicate vapor enters the reaction tube to carry out the vapor deposition for the Ti-MeO—SiO$_2$ composite oxide; further preferably, the alkyl silicate vapor is introduced into the reaction tube using nitrogen to carry out the vapor deposition;

(7) calcining the D obtained in step (6) to obtain a Ti-MeO—SiO$_2$ composite oxide having a SiO$_2$ layer coated on the surface of the composite oxide, this product is referred to as SiO$_2$—Ti-MeO—SiO$_2$;

(8) carrying out a silylanization treatment for the SiO$_2$—Ti-MeO—SiO$_2$ obtained in step (7).

The product codes "A", "B", "C", "D" appeared in the preparation method of the present disclosure do not have special meanings and are used as product codes only for ease of description. The Ti species described herein are terms commonly used in the art, the Ti species comprise tetra coordinate skeletal titanium, free titanium dioxide.

Further, in some specific embodiments, steps (3)-(8) are all carried out in the same reaction tube.

The auxiliary metal salt in step (1) of the present disclosure can be one or more of Ce(NO$_3$)$_3$, Pr(NO$_3$)$_3$, Tb(NO$_3$)$_3$ and La(NO$_3$)$_3$. Using the amount of the metal oxide of the auxiliary metal salt for calculation, the auxiliary metal salt is added in an amount preferably ranging from 0.6-2.4 wt % based on the mass of the silica gel carrier. Said metal oxide refers to an oxide obtained from the decomposition after high-temperature calcination of the auxiliary metal salt, for example, the oxides corresponding to Ce(NO$_3$)$_3$, Pr(NO$_3$)$_3$, Tb(NO$_3$)$_3$ and La(NO$_3$)$_3$ are CeO$_2$, Pr$_6$O$_{11}$, TbO$_2$ and La$_2$O$_3$ respectively.

The impregnation method in step (1) can be an incipient-wetness impregnation method or other impregnation methods, and is not particularly limited as long as the method can load the auxiliary metal salt on the silica gel carrier. The specific operations of loading the auxiliary metal salt using an incipient-wetness impregnation method, for example, can be carried out as follows: first of all, measuring the water absorption per unit mass of the silica gel carrier, calculating the saturated water absorption of the silica gel carrier, and recording the saturated water absorption as a; weighing a certain amount of auxiliary metal salt and dissolving the salt in a grams of water, and recording the water solution as b solution; then evenly spraying b solution on the surface of the silica gel carrier, then allowing to settle, drying specifically, such as allowing to settle for 2-5 hours then drying at 80-120° C.; specific impregnation operations are conventional means in the art, and will not be described in detail.

An auxiliary metal salt is added in step (1) of the present disclosure, and the auxiliary metal salt is preferably one or more of Ce(NO$_3$)$_3$, Pr(NO$_3$)$_3$, Tb(NO$_3$)$_3$ and La(NO$_3$)$_3$. The purpose of adding an auxiliary metal salt is to utilize the alkalinity of the oxide formed from the auxiliary metal salt during the subsequent calcination process, thereby neutralizing the acidity of the free TiO$_2$ which is inevitably produced in step (4) and the subsequent steps, reducing self-decomposition reactions of peroxides and improving catalyst selectivity.

The silica gel carrier used in step (1) of the present disclosure is a C-type silica gel, and the specific shape thereof can be but is not limited to a spherical shape or a block etc., and there's no special requirement for the specific shape, for example, the silica gel can be but is not limited to an irregular blocky C-type silica gel. Preferably, the silica gel carrier used in step (1) has a specific surface area of 100-350 m$^2$/g, an average pore diameter of 8-11 nm, a pore volume of 0.7-1.2 ml/g, a Na$_2$O impurity content of <100 ppm, a Fe$_2$O$_3$ impurity content of <500 ppm and a size of a spherical equivalent diameter of 0.5-2 mm.

The main purpose of drying in step (2) of the present disclosure is to remove free water in the silica gel carrier, preferred drying temperature is 150-240° C. and preferred drying time is 120 min-240 min. Preferably, in step (2), the auxiliary metal salt modified silica gel carrier A obtained in step (1) is dried using a drying gas, and the drying gas used for drying can be any gas that does not react with silica gel, such as air or nitrogen; the drying in step (2) can be carried out specifically in a reaction tube, and the flow rate of the drying gas in the reaction tube is preferably 1.0-3.0 cm/s.

The step (3) of the present disclosure is a chemical vapor deposition, specifically, the chemical vapor deposition of this step can be carried out in a reaction tube. The titanium salt vapor, preferably TiCl$_4$ vapor in the vaporization tank is introduced into the reaction tube using an inert gas, preferably N$_2$. The TiCl$_4$ vapor interacts with the associated hydroxy on the surface of the silica gel to carry out the following reaction:

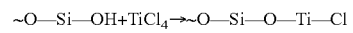

~O—Si—OH+TiCl$_4$→~O—Si—O—Ti—Cl wherein Ti is loaded on the silica gel carrier in an amount ranges from 0.1-5.0 wt %, preferably 2.5-4.5 wt % based on the weight of the silica gel carrier (i.e., the amount of loaded Ti is calculated based on the weight of the silica gel carrier used in step (1)), the Ti described herein is based on the Ti element in the used titanium salt vapor. In some specific embodiments, the titanium salt is contained in a vaporization tank to provide titanium salt vapor, and the titanium salt vapor, preferably TiCl$_4$ vapor has a temperature of 137° C.-150° C., i.e. the titanium salt vapor is preheated to this temperature; the flow rate of the inert gas, preferably N$_2$ in the reaction tube is 0.05-2.0 cm/s, preferably 0.50-1.35 cm/s, the temperature of the reaction between the titanium salt vapor, preferably TiCl$_4$ vapor and the associated hydroxy on the surface of the silica gel is 150-300° C., and the deposition time is 120-240 min.

In some preferred embodiments, the calcination carried out in N$_2$ atmosphere in step (4) of the present disclosure is carried out at a calcination temperature ranges from 450-700° C., preferably 500-600° C., the temperature is increased in a rate ranges from 1.5-3° C./min, and the calcination time is 30-240 min, preferably 120-180 min, the flow rate of N$_2$ is 0.05-2.0 cm/s, preferably 1-2.5 cm/s. The main purpose of calcination is to introduce the Ti species adsorbed on the surface of the silica gel into the silica gel skeleton to form a tetra-coordinated skeletal Ti (or a Ti=O tetrahedron) active center, to stabilize the active center, and some of the Cl elements form HCl gas during calcination process and are removed from the surface of the silica gel carrier.

The step (5) of the present disclosure is water washing, and the purpose thereof is to remove the Cl element adsorbed on the surface of the silica gel carrier using water vapor, reducing or eliminating the influence of Cl element on the performance of the catalyst; the water washing process can be carried out specifically in the reaction tube. Preferably, a certain amount of water vapor is introduced into the reaction tube using an inert gas, preferably N$_2$, and the Cl element on the surface of the silica gel carrier is interacted with the water vapor to form HCl gas to be removed from the surface of the silica gel carrier. In some specific embodiments, the water vapor comes from a vaporization tank, which has a temperature of 100-200° C. (i.e., the water vapor is preheated to this temperature), preferably 120-180° C.; the water washing time is 180-240 min, and the flow rate of the inert gas, preferably N$_2$ is 1-2.5 cm/s. The molar ratio of water vapor to Ti is 20-150:1, preferably 50-100:1, and the amount of Ti in this molar ratio is based on the amount of the Ti element in the titanium salt vapor used in step (3); water washing with a preferred molar ratio of water vapor can remove Cl effectively and completely.

The step (6) of the present disclosure is also a chemical vapor deposition, and the main purpose thereof is to load an alkyl silicate, preferably tetraethyl orthosilicate onto the surface of the silica gel carrier. Preferably, the chemical vapor deposition of this step is carried out in a reaction tube, and an alkyl silicate vapor, preferably tetraethyl orthosilicate vapor is introduced into the reaction tube using an inert gas, preferably $N_2$; in some specific embodiments, the alkyl silicate vapor, preferably tetraethyl orthosilicate vapor comes from a vaporization tank that is heated to a temperature of 166-200° C., the flow rate of the inert gas, preferably $N_2$ in the reaction tube is 0.05-2.0 cm/s, preferably 0.5-1.0 cm/s, the reaction temperature is 166-200° C., the reaction time is 120-180 min, and the weight ratio of alkyl silicate, preferably tetraethyl orthosilicate to silica gel carrier is 0.5-1:1, the weight of the silica gel carrier in this weight ratio is based on the weight of the silica gel carrier used in step (1).

The purpose of the step (7) of the present disclosure is to calcine and remove the ligand alkyl ester in the alkyl silicate in air atmosphere, the ligand alkyl ester forms an oxycarbide and is then removed, a $SiO_2$ film (or a $SiO_2$ layer) is further formed on the surface of the silica gel carrier, and a $SiO_2$—Ti-MeO—$SiO_2$ sandwich structure is formed, which can protect Ti species, reducing (decreasing) the loss (loss rates) of Ti active centers, and improving the stability of the catalyst. In some preferred embodiments, in step (7), the calcination is carried out with a heating rate of 1.5-3° C./min, a calcination temperature of 500-700° C., a calcination time of 30-120 min, and the flow rate of air is 0.5-1 cm/s.

The step (8) of the present disclosure is a silylanization treatment, and the silylanization treatment can be specifically carried out in a reaction tube, a silylanization reagent vapor is introduced into the reaction tube using an inert gas, preferably $N_2$, and the chemical reaction is carried out as follows:

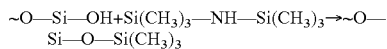

The purpose of the silylanization treatment is to increase the hydrophobicity of the catalyst surface, reducing the decomposition ability of the catalyst to peroxide, and improving the selectivity of the catalyst; the silylanization reagent is preferably hexamethyl disilylamine, hexamethyl disilylamine which is used in an amount of 5 wt %-15 wt % based on the weight of the silica gel carrier (i.e., based on the weight of the silica gel carrier used in step (1)); preferably, the temperature of hexamethyl disilylamine is 126-150° C., the silylanization temperature is 200-300° C., the flow rate of the inert gas, preferably $N_2$ in the reaction tube is 0.5-1 cm/s, and the silylanization time is 60-180 min.

The catalyst prepared by the preparation method of the present disclosure is used for catalyzing propylene epoxidation to prepare propylene oxide. The preferred process conditions are as follows: the reaction temperature is 40-120° C., the pressure is 2-4.5 MPa (gauge pressure), the molar ratio of propylene to ethylbenzene hydroperoxide (EBHP) is 3-10:1, and the mass space velocity is 1-5 $h^{-1}$.

The present disclosure has the following advantageous effects:

(1) A layer of $SiO_2$ is further deposited on the surface of Ti-MeO—$SiO_2$ composite oxide by chemical vapor deposition, a layer of protective $SiO_2$ shell is formed, and a $SiO_2$—Ti-MeO—$SiO_2$ sandwich structure is formed, which can protect Ti species, reducing (decreasing) the loss (loss rates) of Ti active centers, and improving the stability of the catalyst; (2) by modifying the silica gel carrier though adding a metal auxiliary thereto, the metal auxiliary synergizes with Ti active centers to improve the activity and the selectivity to propylene oxide of the catalyst, the average selectivity of the catalyst to PO is up to 96.7%, which reduces the consumption of only propylene of PO products; (3) The process flow of the present disclosure is simple to control, easy to industrialize, and has great prospects for industrialization.

BRIEF DESCRIPTION OF THE DRAWINGS

FIG. 1 is a schematic diagram showing the process flow of a catalyst preparation device.

Description of the reference signs: 1 represents a alkyl silicate vaporization tank, 2 represents a $TiCl_4$ vaporization tank, 3 represents a water and silylanization reagent vaporization tank; 4 represents an exhaust gas absorption tank; and 5 represents a reaction tube.

DETAILED DESCRIPTION

In order to understand the present disclosure better, the present disclosure will be further illustrated below with reference to the embodiments, but the content of the present disclosure is not limited thereto.

The Inductively Coupled Plasma Optical Emission Spectroscopy (ICP-OES) used in the examples of the present disclosure was produced by Agilent Technologies, model 720 ICP-OES;

In the examples of the present disclosure, the content of PO (propylene oxide) in the reaction liquid and the exhaust gas absorption liquid was analyzed by gas chromatography, and the conversion rate of EBHP (ethylbenzene hydroperoxide) was analyzed by iodimetry. The conditions of chromatography are shown in Table 1.

TABLE 1

| Operating conditions of Chromatography | |
|---|---|
| Chromatographic column | Agilent 19091N-133 |
|  | (30 m × 250 μm × 0.25 μm) |
| Flow rate of $H_2$ | 35 mL/min |
| Flow rate of air | 350 mL/min |
| Flow rate of makeup gas ($N_2$) | 25 mL/min |
| Heater | 270° C. |
| Column box | 250° C. |
| Heating procedure | Initial temperature: 50° C. |
|  | Heating program: 50-100° C., |
|  | 15° C./min, maintaining for 0 min, |
|  | 100-250° C., 20° C./min, maintaining |
|  | for 2 min |
| Split ratio of injection port | 30:1 |
| Temperature of FID detector | 270° C. |

The content of PO was determined by internal standard method. The liquid phase concentration was determined using DMF as the solvent and DT (dioxane) as the internal standard substance. The internal standard curve of PO and DT was determined to be y=0.6985x−0.0046, $R^2$=0.999; the concentration of PO in gas phase absorption liquid was determined using toluene as the internal standard substance, the internal standard curve of PO and toluene was determined to be y=2.161x+0.0002, $R^2$=0.999.

Concentration of PO in liquid phase=(0.6985×($A_{PO}$/$A_{DT}$)−0.0046)×0.01×dilution ratio, A represents the peak area, the same below;

Content of PO in liquid phase=concentration of PO in liquid phase×mass of sample in liquid phase;

Concentration of PO in gas phase=(2.162×($A_{PO}$/$A_{toluene}$)+0.0002)×mass of toluene;

Content of PO in gas phase=concentration of PO in gas phase×total amount of absorption liquid/amount of sample in gas phase;

Total production amount of PO=content of PO in gas phase+content of PO in liquid phase;

Selectivity to PO=total production amount of PO/amount of PO theoretically produced from propylene oxidized by EBHP (ethylbenzene hydroperoxide)×100%.

The conversion rate of EBHP was titrated by iodimetry and measured by a titrator.

Conversion rate of EBHP=(initial value of EBHP−residual amount of EBHP)/initial value of EBHP.

Residual amount of EBHP=(titration end point−blank)× $C_{Na_2S_2O_3}$×0.001×0.5×142×total amount of liquid sample/sample amount for titration, wherein $C_{Na_2S_2O_3}$ is the concentration of sodium thiosulfate.

The silica gel carrier used in the examples or the comparative examples is an irregular blocky C-type silica gel carrier, which is provided by Qingdao GuiChuang Fine Chemical Co., Ltd., and has a silica gel particle size (spherical equivalent diameter) of 0.6-1.1 mm, a specific surface area of 256 m$^2$/g, an average pore diameter of 9.2 nm, a pore volume of 0.94 ml/g, a water absorption rate of 1.12 g water/g of silica gel (saturated water absorption), a $Na_2O$ impurity content of 89 ppm and a $Fe_2O_3$ impurity content of 327 ppm.

The process conditions for propylene epoxidation to produce propylene oxide in the examples and comparative examples are as follows: the oxidant is ethylbenzene hydroperoxide (EBHP), the reaction tube is a fixed bed reactor with an inner diameter of 24 mm, and the catalyst is loaded in an amount of 10 g; the molar ratio of propylene to EBHP is 5:1, the mass space velocity is 4 h$^{-1}$; the initial reaction temperature is 50° C., and the reaction temperature is gradually increased according to the conversion rate of EBHP (the conversion rate of EBHP was guaranteed to be >99%).

Example 1

0.36 g of $Ce(NO_3)_3$ was weighed and dissolved in 33.6 g of distilled water, sprayed onto 30 g of silica gel carrier, to settle for 2 hours and then dried at 80° C. The product obtained in this step was called auxiliary metal salt modified silica gel carrier A (or referred to as product A or A for short).

As shown in FIG. 1, the silica gel carrier on which $Ce(NO_3)_3$ was loaded (i.e., product A) was charged into reaction tube 5 and dried at 180° C. for 120 min in $N_2$ atmosphere, and the linear velocity of $N_2$ in reaction tube 5 was 1.2 cm/s. Dried A was obtained in this step.

Chemical vapor deposition of $TiCl_4$: 2.98 g of $TiCl_4$ was added to $TiCl_4$ vaporization tank 2 which was then heated at a temperature of 137° C., $TiCl_4$ vapor was introduced into reaction tube 5 using $N_2$ to react with the silica gel, the linear velocity of $N_2$ in reaction tube 5 was 0.5 cm/s, the deposition time was 120 min (the reaction temperature of this step was the same as the drying temperature in the previous step, which was 180° C.); the product obtained in this step was called auxiliary metal salt and $TiCl_4$ loaded silica gel B (referred to as silica gel B or B for short).

Calcination: the temperature was raised to 500° C. at a heating rate of 2° C./min, the linear velocity of $N_2$ in reaction tube 5 was 1 cm/s, and the silica gel B was calcined for 120 min; the product obtained in this step was called auxiliary metal oxide and Ti species loaded silica gel C (or referred to as C for short).

Water washing: 14.1 g of distilled water was added to water and silylanization reagent vaporization tank 3 which was then heated at a temperature of 120° C., water vapor was introduced into reaction tube 5 using $N_2$ for water washing the obtained silica gel C, the linear velocity of $N_2$ in the reaction tube was 1 cm/s and the water washing time was 180 min; the product obtained by water vapor washing was referred to as a Ti-MeO—$SiO_2$ composite oxide.

Chemical vapor deposition of alkyl silicate: 15 g of tetraethyl orthosilicate was added to alkyl silicate vaporization tank 1 which was then heated at a temperature of 166° C., tetraethyl orthosilicate vapor was introduced into the reaction tube using $N_2$ to react with the silica gel, the linear velocity of $N_2$ in the reaction tube was 0.5 cm/s, and the deposition time was 120 min (the reaction temperature of this step was the same as the temperature at which the alkyl silicate vaporization tank was heated, which was 166° C.); the product obtained in this step was called a Ti-MeO—$SiO_2$ composite oxide D having a silicon-containing compound loaded on the surface of the composite oxide (or referred to as product D);

Calcination: the temperature was raised to 500° C. at a heating rate of 3° C./min, the linear velocity of air in the reaction tube was 0.5 cm/s, and the product D was calcined for 120 min; a product having a $SiO_2$ layer coated on the surface was obtained by calcination, the product was called a Ti-MeO—$SiO_2$ composite oxide having a $SiO_2$ layer coated on the surface, or is referred to as $SiO_2$—Ti-MeO—$SiO_2$.

Silylanization treatment: 4.5 g of hexamethyl disilylamine was added to water and silylanization reagent vaporization tank 3 which was then heated at a temperature of 130° C., the hexamethyl disilylamine vapor was introduced into the reaction tube using $N_2$ to react with the silica gel (the silica gel refers to the product obtained by calcination, $SiO_2$—Ti-MeO—$SiO_2$), the linear velocity of $N_2$ in the reaction tube was 1 cm/s, the silylanization temperature was 200° C., and the silylanization time was 180 min; the obtained catalyst is referred to as TS-C1.

Exhaust gas absorption tank 4 was used for absorbing $TiCl_4$ that was not loaded on the carrier and HCl gas generated during the calcination and water washing procedure.

The TS-C1 was evaluated. The catalyst was used for propylene epoxidation to produce propylene oxide, operated continuously for 1000 hr, the reaction temperature was raised from the initial 50° C. to 80° C., and sampled for gas chromatography analysis. The EBHP conversion rate was >99.9%, the highest selectivity to PO reached 96.4%, the average selectivity reached 95.2%. The product was collected for ICP-OES analysis and no catalyst component Ti was found.

Example 2

0.48 g of $Pr(NO_3)_3$ was weighed and dissolved in 33.6 g of distilled water, sprayed onto 30 g of silica gel carrier, allowed to settle for 2 hours and then dried at 80° C.

As shown in FIG. 1, the silica gel carrier on which $Pr(NO_3)_3$ was loaded was charged into a reaction tube and dried at 200° C. for 180 min in $N_2$ atmosphere, and the linear velocity of $N_2$ in the reaction tube was 1.6 cm/s.

Chemical vapor deposition of $TiCl_4$: 3.57 g of $TiCl_4$ was added to a $TiCl_4$ vaporization tank which was then heated at a temperature of 140° C., $TiCl_4$ vapor was introduced into the reaction tube using $N_2$ to react with the silica gel, the linear velocity of $N_2$ in the reaction tube was 0.7 cm/s, the deposition time was 180 min (the reaction temperature of this step was the same as the drying temperature in the previous step, which was 200° C.);

Calcination: the temperature was raised to 550° C. at a heating rate of 2° C./min, the linear velocity of $N_2$ in the reaction tube was 1.5 cm/s, the calcination lasted for 180 min;

Water washing: 26.7 g of distilled water was added to a water and silylanization reagent vaporization tank which was then heated at a temperature of 140° C., water vapor was introduced into the reaction tube using $N_2$ for water washing, the linear velocity of $N_2$ in the reaction tube was 1.5 cm/s and the water washing time was 180 min;

Chemical vapor deposition of alkyl silicate: 21 g of tetraethyl orthosilicate was added to a alkyl silicate vaporization tank which was then heated at a temperature of 170° C., tetraethyl orthosilicate vapor was introduced into the reaction tube using $N_2$ to react with the silica gel, the linear velocity of $N_2$ in the reaction tube was 0.8 cm/s, and the deposition time was 150 min (the reaction temperature of this step was the same as the temperature at which the alkyl silicate vaporization tank was heated, which was 170° C.);

Calcination: the temperature was raised to 550° C. at a heating rate of 3° C./min, the linear velocity of air in the reaction tube was 0.7 cm/s, the calcination lasted for 60 min;

Silylanization treatment: 3 g of hexamethyl disilylamine was added to a water and silylanization reagent vaporization tank which was then heated at a temperature of 135° C., hexamethyl disilylamine vapor was introduced into the reaction tube using $N_2$ to react with the silica gel, the linear velocity of $N_2$ in the reaction tube was 0.7 cm/s, the silylanization temperature was 200° C., and the silylanization time was 150 min; the obtained catalyst was referred to as TS-C2.

The TS-C2 was evaluated. The catalyst was used for propylene epoxidation to produce propylene oxide, operated continuously for 1550 hr, the reaction temperature was raised from the initial 50° C. to 85° C., and sampled for gas chromatography analysis. The EBHP conversion rate was >99.9%, the highest selectivity to PO reached 96.7%, the average selectivity reached 95.1%. The product was collected for ICP-OES analysis and no catalyst component Ti was found.

Example 3

0.6 g of $Tb(NO_3)_3$ was weighed and dissolved in 33.6 g of distilled water, sprayed onto 30 g of silica gel carrier, allowed to settle for 2 hours and then dried at 80° C.

As shown in FIG. 1, the silica gel carrier on which $Tb(NO_3)_3$ was loaded was charged into a reaction tube and dried at 240° C. for 240 min in $N_2$ atmosphere, and the linear velocity of $N_2$ in the reaction tube was 2 cm/s.

Chemical vapor deposition of $TiCl_4$: 4.17 g of $TiCl_4$ was added to a $TiCl_4$ vaporization tank which was then heated at a temperature of 145° C., $TiCl_4$ vapor was introduced into the reaction tube using $N_2$ to react with the silica gel, the linear velocity of $N_2$ in the reaction tube was 0.8 cm/s, the deposition time was 200 min (the reaction temperature of this step was the same as the drying temperature in the previous step, which was 240° C.);

Calcination: the temperature was raised to 600° C. at a heating rate of 2° C./min, the linear velocity of $N_2$ in the reaction tube was 2 cm/s, the calcination lasted for 200 min;

Water washing: 33.5 g of distilled water was added to a water and silylanization reagent vaporization tank which was then heated at a temperature of 160° C., water vapor was introduced into the reaction tube using $N_2$ for water washing, the linear velocity of $N_2$ in the reaction tube was 2 cm/s and the water washing time was 200 min;

Chemical vapor deposition of alkyl silicate: 27 g of tetraethyl orthosilicate was added to a alkyl silicate vaporization tank which was then heated at a temperature of 180° C., tetraethyl orthosilicate vapor was introduced into the reaction tube using $N_2$ to react with the silica gel, the linear velocity of $N_2$ in the reaction tube was 0.9 cm/s, and the deposition time was 180 min (the reaction temperature of this step was the same as the temperature at which the alkyl silicate vaporization tank was heated, which was 180° C.);

Calcination: the temperature was raised to 600° C. at a heating rate of 3° C./min, the linear velocity of air in the reaction tube was 0.8 cm/s, the calcination lasted for 60 min;

Silylanization treatment: 2.4 g of hexamethyl disilylamine was added to a water and silylanization reagent vaporization tank which was then heated at a temperature of 140° C., hexamethyl disilylamine vapor was introduced into the reaction tube using $N_2$ to react with the silica gel, the linear velocity of $N_2$ in the reaction tube was 0.5 cm/s, the silylanization temperature was 250° C., and the silylanization time was 120 min; the obtained catalyst was referred to as TS-T3.

The TS-T3 was evaluated. The catalyst was used for propylene epoxidation to produce propylene oxide, operated continuously for 1800 hr, the reaction temperature was raised from the initial 50° C. to 90° C., and sampled for gas chromatography analysis. The EBHP conversion rate was >99.9%, the highest selectivity to PO reached 97.8%, the average selectivity reached 96.7%. The product was collected for ICP-OES analysis and no catalyst component Ti was found.

Example 4

0.72 g of $La(NO_3)_3$ was weighed and dissolved in 33.6 g of distilled water, sprayed onto 30 g of silica gel carrier, allowed to settle for 2 hours and then dried at 80° C.

As shown in FIG. 1, the silica gel carrier on which $La(NO_3)_3$ was loaded was charged into a reaction tube and dried at 220° C. for 120 min in $N_2$ atmosphere, and the linear velocity of $N_2$ in the reaction tube was 2.5 cm/s.

Chemical vapor deposition of $TiCl_4$: 5.36 g of $TiCl_4$ was added to a $TiCl_4$ vaporization tank which was then heated at a temperature of 150° C., $TiCl_4$ vapor was introduced into the reaction tube using $N_2$ to react with the silica gel, the linear velocity of $N_2$ in the reaction tube was 1.35 cm/s, the deposition time was 240 min (the reaction temperature of this step was the same as the drying temperature in the previous step, which was 220° C.);

Calcination: the temperature was raised to 550° C. at a heating rate of 2° C./min, the linear velocity of $N_2$ in the reaction tube was 2.5 cm/s, and the calcination lasted for 240 min;

Water washing: 50.7 g of distilled water was added to a water and silylanization reagent vaporization tank which was then heated at a temperature of 180° C., water vapor was introduced into the reaction tube using $N_2$ for water washing, the linear velocity of $N_2$ in the reaction tube was 2.5 cm/s and the water washing time was 240 min;

Chemical vapor deposition of alkyl silicate: 30 g of tetraethyl orthosilicate was added to a alkyl silicate vaporization tank which was then heated at a temperature of 200° C., the tetraethyl orthosilicate vapor was introduced into the reaction tube using $N_2$ to react with the silica gel, the linear velocity of $N_2$ in the reaction tube was 1 cm/s, and the deposition time was 180 min (the reaction temperature of this step was the same as the temperature at which the alkyl silicate vaporization tank was heated, which was 200° C.);

Calcination: the temperature was raised to 700° C. at a heating rate of 3° C./min, the linear velocity of air in the reaction tube was 1 cm/s, the calcination lasted for 30 min;

Silylanization treatment: 1.8 g of hexamethyl disilylamine was added to a water and silylanization reagent vaporization tank which was then heated at a temperature of 150° C., hexamethyl disilylamine vapor was introduced into the reaction tube using $N_2$ to react with the silica gel, the linear velocity of $N_2$ in the reaction tube was 0.6 cm/s, the silylanization time was 150 min; the silylanization temperature was 300° C., the obtained catalyst was referred to as TS-L4.

The TS-L4 was evaluated. The catalyst was used for propylene epoxidation to produce propylene oxide, operated continuously for 1200 hr, the reaction temperature was raised from the initial 50° C. to 75° C., and sampled for gas chromatography analysis. The EBHP conversion rate was >99.9%, the highest selectivity to PO reached 96.8%, the average selectivity reached 95.6%. The product was collected for ICP-OES analysis and no catalyst component Ti was found.

Comparative Example 1

0.6 g of $Tb(NO_3)_3$ was weighed and dissolved in 33.6 g of distilled water, sprayed onto 30 g of silica gel carrier, allowed to settle for 2 hours and then dried at 80° C.

The silica gel carrier on which $Tb(NO_3)_3$ was loaded was charged into the reaction tube and dried at 240° C. for 240 min in $N_2$ atmosphere, and the linear velocity of $N_2$ in the reaction tube was 2 cm/s.

Chemical vapor deposition of $TiCl_4$: 4.17 g of $TiCl_4$ was added to a $TiCl_4$ vaporization tank which was then heated at a temperature of 145° C., $TiCl_4$ vapor was introduced into the reaction tube using $N_2$ to react with the silica gel, the linear velocity of $N_2$ in the reaction tube was 0.8 cm/s, the deposition time was 200 min (the reaction temperature of this step was the same as the drying temperature in the previous step, which was 240° C.);

Calcination: the temperature was raised to 600° C. at a heating rate of 2° C./min, the linear velocity of $N_2$ in the reaction tube was 2 cm/s, and calcination lasted for 200 min;

Water washing: 33.5 g of distilled water was added to a water and silylanization reagent vaporization tank which was then heated at a temperature of 160° C., water vapor was introduced into the reaction tube using $N_2$ for water washing, the linear velocity of $N_2$ in the reaction tube was 2 cm/s and the water washing time was 200 min;

Silylanization treatment: 2.4 g of hexamethyl disilylamine was added to a water and silylanization reagent vaporization tank which was then heated at a temperature of 140° C., the hexamethyl disilylamine vapor was introduced into the reaction tube using $N_2$ to react with the silica gel, the linear velocity of $N_2$ in the reaction tube was 0.5 cm/s, the silylanization temperature was 250° C., and the silylanization time was 120 min; the obtained catalyst was referred to as TS-B4.

The TS-B4 was evaluated. The catalyst was used for propylene epoxidation to produce propylene oxide, operated continuously for 750 hr, the reaction temperature was raised from the initial 50° C. to 80° C., and sampled for gas chromatography analysis. The EBHP conversion rate was >99.9%, the highest selectivity to PO reached 97.5%, the average selectivity reached 95.7%. The product was collected for ICP-OES analysis, the content of the catalyst component Ti in the product was about 313 ppm; the Ti content in the fresh catalyst was about 3.42%, the Ti content in the catalyst after evaluation was about 2.61%, and the loss rate reached 23.7%.

Comparative Example 2

30 g of silica gel carrier was weighed and charged into the reaction tube and dried at 240° C. for 240 min in $N_2$ atmosphere, and the linear velocity of $N_2$ in the reaction tube was 2 cm/s.

Chemical vapor deposition of $TiCl_4$: 4.17 g of $TiCl_4$ was added to a $TiCl_4$ vaporization tank which was then heated at a temperature of 145° C., the $TiCl_4$ vapor was introduced into the reaction tube using $N_2$ to react with the silica gel, the linear velocity of $N_2$ in the reaction tube was 0.8 cm/s, the deposition time was 200 min (the reaction temperature of this step was the same as the drying temperature in the previous step, which was 240° C.);

Calcination: the temperature was raised to 600° C. at a heating rate of 2° C./min, the linear velocity of $N_2$ in the reaction tube was 2 cm/s, the calcination lasted for 200 min;

Water washing: 33.5 g of distilled water was added to a water and silylanization reagent vaporization tank which was then heated at a temperature of 160° C., the water vapor was introduced into the reaction tube using $N_2$ for water washing, the linear velocity of $N_2$ in the reaction tube was 2 cm/s and the water washing time was 200 min;

Chemical vapor deposition of alkyl silicate: 27 g of tetraethyl orthosilicate was added to a alkyl silicate vaporization tank which was then heated at a temperature of 180° C., tetraethyl orthosilicate vapor was introduced into the reaction tube using $N_2$ to react with the silica gel, the linear velocity of $N_2$ in the reaction tube was 0.9 cm/s, and the deposition time was 180 min (the reaction temperature of this step was the same as the temperature at which the alkyl silicate vaporization tank was heated, which was 180° C.);

Calcination: the temperature was raised to 600° C. at a heating rate of 3° C./min, the linear velocity of air in the reaction tube was 0.8 cm/s, the calcination lasted for 60 min;

Silylanization treatment: 2.4 g of hexamethyl disilylamine was added to a water and silylanization reagent vaporization tank which was then heated at a temperature of 140° C., hexamethyl disilylamine vapor was introduced into the reaction tube using $N_2$ to react with the silica gel, the linear velocity of $N_2$ in the reaction tube was 0.5 cm/s, the silylanization temperature was 250° C., and the silylanization time was 120 min; the obtained catalyst was referred to as TS-01.

The TS-01 was evaluated. The catalyst was used for propylene epoxidation to produce propylene oxide, operated continuously for 1500 hr, the reaction temperature was raised from the initial 50° C. to 100° C., and sampled for gas chromatography analysis. The EBHP conversion rate was >99.9%, the highest selectivity to PO reached 94.6%, the average selectivity reached 92.1%. The product was collected for ICP-OES analysis and no catalyst component Ti was found.

Comparative Example 3

30 g of silica gel carrier was weighed and charged into the reaction tube and dried at 240° C. for 240 min in $N_2$ atmosphere, and the linear velocity of $N_2$ in the reaction tube was 2 cm/s.

Chemical vapor deposition of $TiCl_4$: 4.17 g of $TiCl_4$ was added to a $TiCl_4$ vaporization tank which was then heated to a temperature of 145° C., $TiCl_4$ vapor was introduced into the reaction tube using $N_2$ to react with the silica gel, the linear velocity of $N_2$ in the reaction tube was 0.8 cm/s, the deposition time was 200 min (the reaction temperature was the same as the drying temperature in the previous step, which was 200° C.);

Calcination: the temperature was raised to 600° C. at a heating rate of 2° C./min, the linear velocity of $N_2$ in the reaction tube was 2 cm/s, and the calcination lasted for 200 min;

Water washing: 33.5 g of distilled water was added to a water and silylanization reagent vaporization tank which was then heated at a temperature of 160° C., the water vapor was introduced into the reaction tube using $N_2$ for water washing, the linear velocity of $N_2$ in the reaction tube was 2 cm/s and the water washing time was 200 min;

Calcination: the temperature was raised to 600° C. at a heating rate of 3° C./min, the linear velocity of air in the reaction tube was 0.8 cm/s, the calcination lasted for 60 min;

Silylanization treatment: 2.4 g of hexamethyl disilylamine was added to a water and silylanization reagent vaporization tank which was then heated at a temperature of 140° C., hexamethyl disilylamine vapor was introduced into the reaction tube using $N_2$ to react with the silica gel, the linear velocity of $N_2$ in the reaction tube was 0.5 cm/s, the silylanization temperature was 250° C., and the silylanization time was 120 min; the obtained catalyst was referred to as TS-02.

The TS-02 was evaluated. The catalyst was used for propylene epoxidation to produce propylene oxide, operated continuously for 620 hr, the reaction temperature was raised from the initial 50° C. to 95° C., and sampled for gas chromatography analysis. The EBHP conversion rate was >99.9%, the highest selectivity to PO reached 93.6%, the average selectivity reached 91.1%; the Ti content in the fresh catalyst was about 3.45%, the product was collected for ICP-OES analysis, the Ti content in the catalyst after evaluation was about 2.56%, and the loss rate reached 25.8%.

The experimental results of the examples and the comparative examples show that the catalysts prepared by the preparation methods of the present disclosure had good catalyst stabilities during use, the activities and selectivities of the catalysts did not change significantly during the observation time, and the activities were stable; Ti element was not found in the product of each example, indicating that the active component in the catalyst was not lost. It can be seen that the catalysts prepared by the preparation methods of the present disclosure can reduce the loss of the Ti active centers during use, the catalyst activities were stable, the service lives of the catalysts were improved; and the catalysts had high selectivities to PO.

The invention claimed is:

1. A preparation method for an olefin epoxidation catalyst, which comprises the following steps: (1) loading an auxiliary metal salt onto a silica gel carrier to obtain an auxiliary metal salt modified silica gel carrier A; (2) carrying out a drying treatment for the A obtained in step (1); (3) carrying out a chemical vapor deposition for the dried A using a titanium salt vapor to obtain a silica gel B on which the auxiliary metal salt and the titanium salt, are loaded; (4) calcining the B obtained in step (3) to obtain a silica gel C on which the auxiliary metal salt and Ti species are loaded; (5) carrying out a water vapor washing for the C obtained in step (4) to obtain a Ti-MeO—$SiO_2$ composite oxide; (6) carrying out a vapor deposition for the Ti-MeO—$SiO_2$ composite oxide using an alkyl silicate vapor to obtain the Ti-MeO—$SiO_2$ composite oxide D having a silicon-containing compound loaded on the surface of the composite oxide (7) calcining the D obtained in step (6) to obtain a Ti-MeO—$SiO_2$ composite oxide having a SiO2 layer coated on the surface of the composite oxide, which is referred to as SiO2—Ti-MeO—SiO2; (8) carrying out a silylanization treatment for the SiO2—Ti-MeO—SiO2 obtained in step (7), wherein the auxiliary metal salt in the step (1) is selected from the group consisting of $Ce(NO3)_3$, $Pr(NO_3)_3$, $Tb(NO_3)_3$, $La(NO_3)_3$, and combinations thereof.

2. The method according to claim 1, wherein in step (1) the auxiliary metal salt is added in an amount ranging from 0.6-2.4 wt % based on the mass of the silica gel carrier.

3. The method according to claim 1, wherein the silica gel carrier used in step (1) is a C-type silica gel.

4. The method according to claim 3, wherein the silica gel carrier used in step (1) has a spherical shape or is a block C-type silica gel.

5. The method according to claim 3, wherein the silica gel carrier used in step (1) is an irregular blocky C-type silica gel.

6. The method according to claim 3, wherein the silica gel carrier used in step (1) has a specific surface area of 100-350 m2/g, an average pore diameter of 8-11 nm, a pore volume of 0.7-1.2 ml/g, a Na2O impurity content of <100 ppm, a Fe2O3 impurity content of <500 ppm and a size of a spherical equivalent diameter of 0.5-2 mm.

7. The method according to claim 1, wherein in step (2), the drying temperature is 150-240° C. and drying time is 120 min-240 min.

8. The method according to claim 1, wherein based on the weight of the silica gel carrier used in step (1), in step (3), Ti is loaded on the silica gel carrier in an amount ranges from 0.1-5.0 wt %.

9. The method according to claim 8, wherein Ti is loaded on the silica gel carrier in an amount from 2.5-4.5 wt %.

10. The method according to claim 8, wherein the chemical vapor deposition of step (3) is carried out in a reaction tube, the dried A is charged in the reaction tube, an inert gas is used to introduce the titanium salt vapor into the reaction tube, the inert gas has a flow rate of 0.05-2.0 cm/s, the chemical vapor deposition temperature of the reaction is 150-300° C., and the chemical vapor deposition time is 120-240 min.

11. The method according to claim 1, wherein the calcination in step (4) is carried out in a $N_2$ atmosphere, at a temperature ranging from 450-700° C. a time ranging from 30-240 min, and the flow rate of $N_2$ is 0.05-2.0 cm/s.

12. The method according to claim 1, wherein the water vapor used for water vapor washing in step (5) has a temperature of 100-200° C.; based on the amount of the Ti element in the titanium salt vapor used in step (3), the molar ratio of the water vapor to Ti is 20-150:1, the water vapor washing time is 180-240 min.

13. The method according to claim 12, wherein the water vapor used for water vapor washing in step (5) has a temperature of 120-180° C., and based on the amount of the Ti element in the titanium salt vapor used in step (3), the molar ratio of the water vapor to Ti is 50-100:1.

14. The method according to claim 12, wherein the water vapor washing of step (5) is carried out in a reaction tube, water vapor is introduced into the reaction tube using an inert gas at a flow rate of 1-2.5 cm/s.

15. The method according to claim 1, wherein the alkyl silicate vapor used in step (6) is heated to a temperature of 166-200° C.; the vapor deposition of step (6) is carried out in a reaction tube, and the alkyl silicate vapor is introduced into the reaction tube using an inert gas; the flow rate of the inert gas in the reaction tube is 0.05-2.0 cm/s, the reaction temperature is 166-200° C., the deposition time is 120-180 min, and the weight ratio of alkyl silicate to the silica gel carrier used in step (1) is 0.5-1:1.

16. The method according to claim 1, wherein the calcination in step (7) is carried out in air atmosphere at a temperature of 500-700° C., with a calcination time of 30-120 min, and the flow rate of air is 0.5-1 cm/s.

17. The method according to claim 1, wherein the silylanization reagent used for the silylanization treatment in step (8) is hexamethyl disilylamine, based on the weight of the silica gel carrier used in step (1), hexamethyl disilylamine is used in an amount of 5 wt %-15 wt %; the temperature of hexamethyl disilylamine used in step (8) is 126-150° C.; the silylanization treatment is carried out in a reaction tube, the silylanization reagent is introduced into the reaction tube using an inert gas, the flow rate of the inert gas in the reaction tube is 0.5-1 cm/s, the silylanization temperature is 200-300° C., and the silylanization time is 60-180 min.

18. A method for catalyzing propylene epoxidation to prepare propylene oxide, comprising contacting a feed with the catalyst prepared by the method according to claim 1 and recovering the propylene oxide.

19. The method according to claim 18, wherein the contacting conditions for catalyzing propylene epoxidation to prepare propylene oxide are as follows: a reaction temperature of 40-120° C., a gauge pressure of 2-4.5 MPa, a molar ratio of propylene to ethylbenzene hydroperoxide of 3-10:1 and a mass space velocity of 1-5 $h^{-1}$.

20. The method according to claim 1, wherein the titanium salt vapor is $TiCl_4$ vapor.

* * * * *